(12) United States Patent
Archibald et al.

(10) Patent No.: US 6,245,022 B1
(45) Date of Patent: Jun. 12, 2001

(54) NON-INVASIVE BLOOD PRESSURE SENSOR WITH MOTION ARTIFACT REDUCTION AND CONSTANT GAIN ADJUSTMENT DURING PRESSURE PULSES

(75) Inventors: G. Kent Archibald, Vadnais Heights; Timothy G. Curran, Ramsey; Orland H. Danielson, Roseville; Marius O. Poliac, St. Paul; Roger C. Thede, Afton, all of MN (US)

(73) Assignee: Medwave, Inc., Arden Hills, MN (US)

( * ) Notice: Subject to any disclaimer, the term of this patent is extended or adjusted under 35 U.S.C. 154(b) by 0 days.

(21) Appl. No.: 09/343,903

(22) Filed: Jun. 30, 1999

Related U.S. Application Data

(63) Continuation-in-part of application No. 09/174,164, filed on Oct. 16, 1998, now Pat. No. 6,132,382.

(51) Int. Cl.$^7$ .......................................... A61B 5/00
(52) U.S. Cl. ........................................ 600/485; 600/500
(58) Field of Search ................... 600/485, 490, 600/493–496, 500, 503

(56) References Cited

U.S. PATENT DOCUMENTS

| | | | |
|---|---|---|---|
| 4,409,983 | * 10/1983 | Albert | 600/503 |
| 5,241,964 | 9/1993 | McQuilkin | 128/672 |
| 5,450,852 | 9/1995 | Archibald et al. | 128/672 |
| 5,494,043 | * 2/1996 | O'Sullivan et al. | 600/500 |
| 5,640,964 | 6/1997 | Archibal et al. | 128/672 |
| 5,642,733 | 7/1997 | Archibald et al. | 128/672 |
| 5,649,542 | 7/1997 | Archibald et al. | 128/681 |
| 5,720,292 | 2/1998 | Poliac | 128/672 |
| 5,722,414 | 3/1998 | Archibald et al. | 128/672 |
| 5,738,103 | 4/1998 | Poliac | 128/672 |
| 5,749,366 | * 5/1998 | Odagiri et al. | 600/500 |
| 5,797,850 | 8/1998 | Archibald et al. | 600/494 |
| 5,832,924 | 11/1998 | Archibald et al. | 128/672 |
| 5,971,930 | * 10/1999 | Elghazzawi | 600/500 |

* cited by examiner

Primary Examiner—Robert L. Nasser
(74) Attorney, Agent, or Firm—Kinney & Lange, P.A.

(57) ABSTRACT

A non-invasive blood pressure sensor includes a first fluid filled sensing chamber having a diaphragm. A first transducer is fluidly coupled to the first sensing chamber to sense fluid pressure within the first chamber. A flexible body conformable wall surrounds the sensing chamber. The wall applies force to the artery while preventing pressure in a direction generally parallel to the artery from being applied to the sensing chamber. The flexible body conformable wall includes a second fluid filled chamber. A second transducer fluidly coupled to the second chamber senses fluid pressure within the second chamber. As varying pressure is applied to the artery pressure waveforms are sensed by the first transducer. Using output signals of the first and second transducers, the sensed pressure waveform data is analyzed to derive waveform parameters from which blood pressure values are derived. The effects of motion artifacts are reduced by the use of signals from both the first and second transducers. Part of the analysis of the waveform data includes the use of an adjusted gain that is substantially constant during pressure pulses, but that may vary from pulse to pulse. Signal values obtained from the second transducer are multiplied by the adjusted gain.

20 Claims, 12 Drawing Sheets

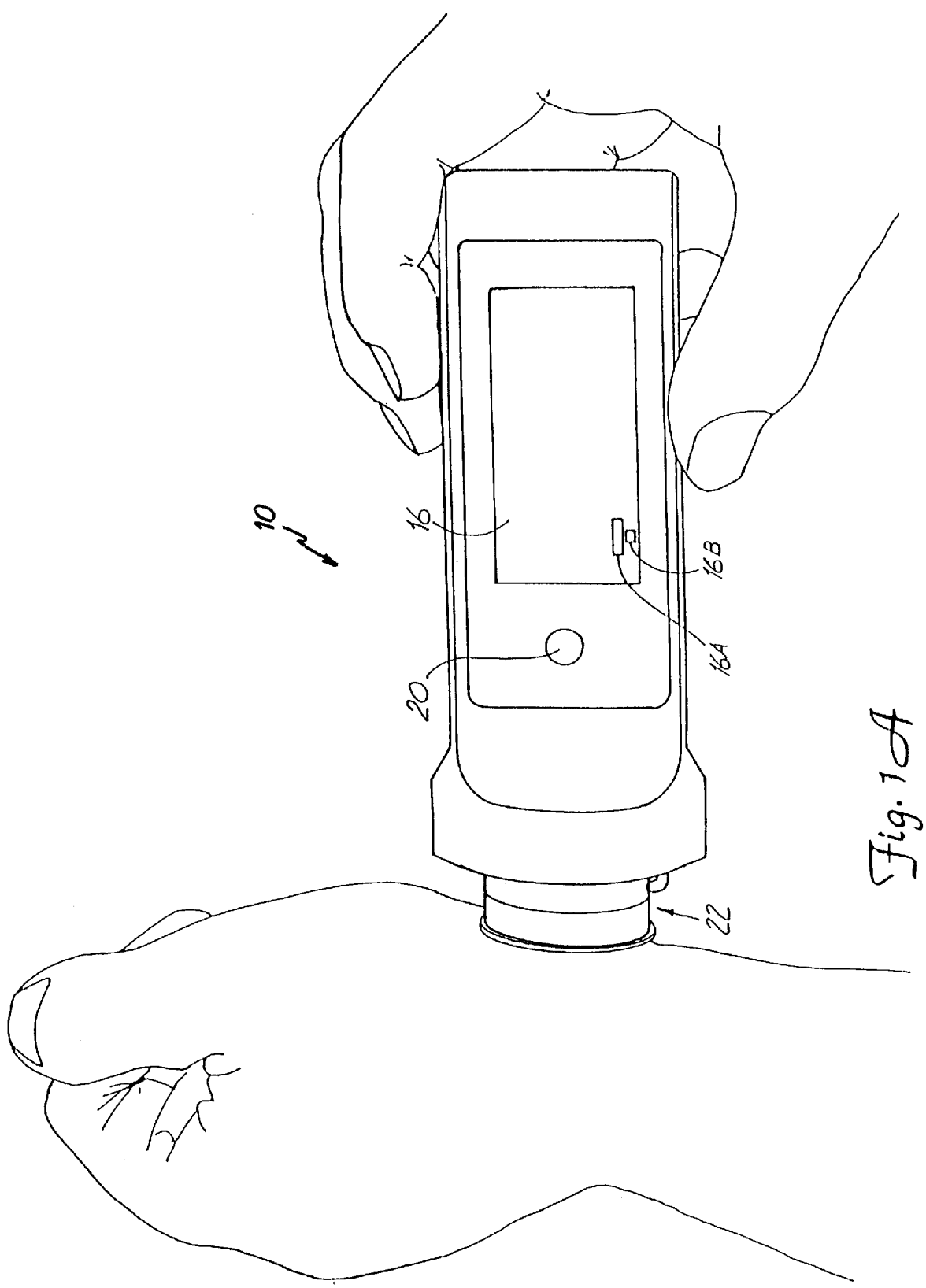

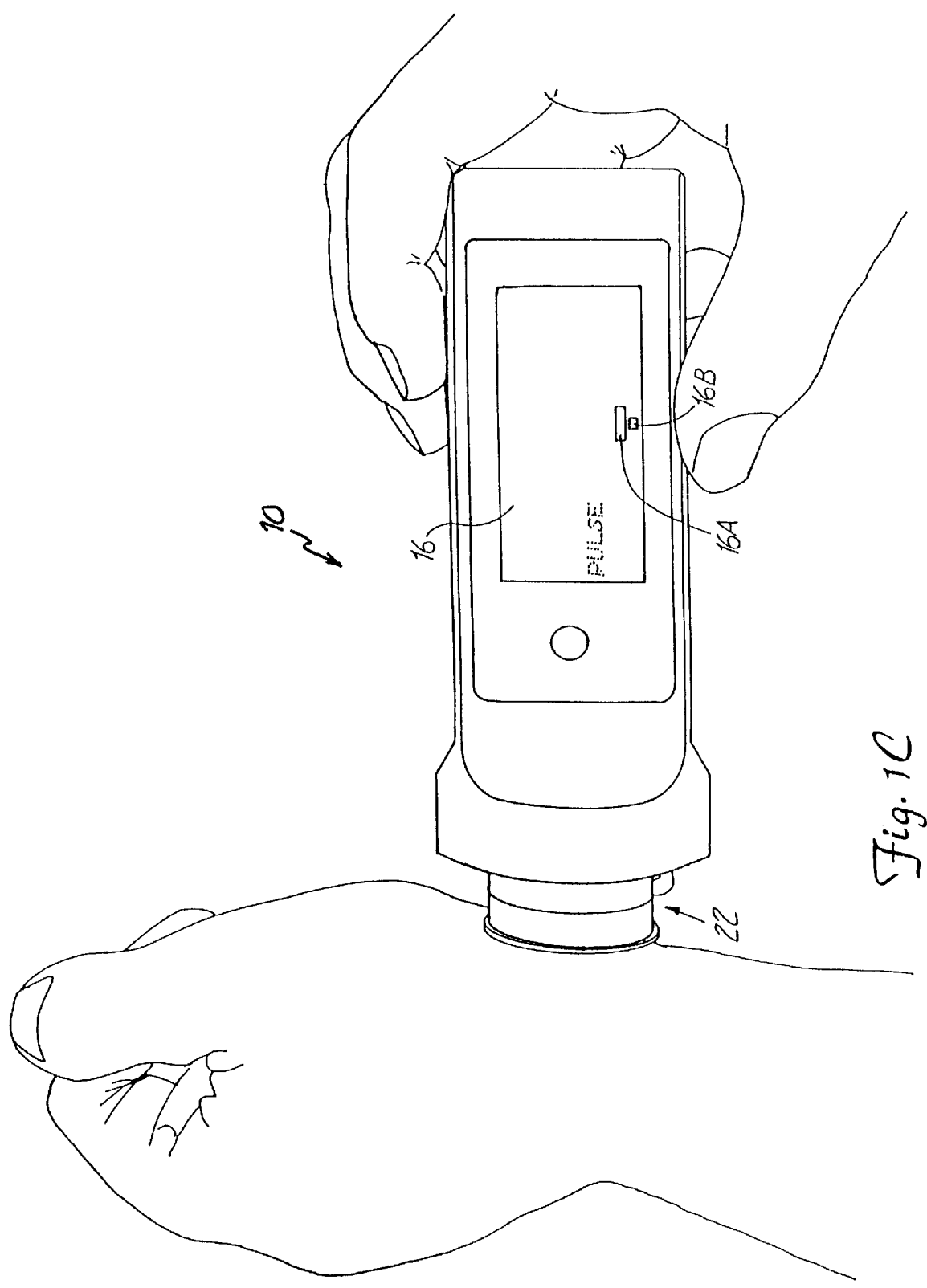

NON-INVASIVE BLOOD PRESSURE SENSOR WITH MOTION ARTIFACT REDUCTION AND CONSTANT GAIN ADJUSTMENT DURING PRESSURE PULSES

CROSS-REFERENCE TO RELATED APPLICATION(S)

This application is a continuation-in-part of commonly assigned and U.S. patent application Ser. No. 09/174,164, filed Oct. 16, 1998, entitled "NON-INVASIVE BLOOD PRESSURE SENSOR WITH MOTION ARTIFACT REDUCTION" now U.S. Pat. No. 6,132,382.

BACKGROUND OF THE INVENTION

The present invention relates to systems and devices for measuring arterial blood pressure. In particular, the invention relates to an improved method and device for measuring arterial blood pressure in a non-invasive manner while reducing the effects of motion artifacts using a constant gain adjustment during pressure pulses.

There has been a continuing need for devices which will measure blood pressure non-invasively, with accuracy comparable to invasive methods. Medwave, Inc. the assignee of the present invention, has developed non-invasive blood pressure measurement devices which are described in the following United States patents: U.S. Pat. No. 5,649,542 entitled CONTINUOUS NONINVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; and U.S. Pat. No. 5,797,850 entitled METHOD AND APPARATUS FOR CALCULATING BLOOD PRESSURE OF AN ARTERY. Further description of these devices is found in United States patent application Ser. No. 08/912,139 filed Aug. 15, 1997, entitled HAND-HELD NON-INVASIVE BLOOD PRESSURE MEASUREMENT DEVICE.

As described in these patents and the pending patent application, the Medwave non-invasive blood pressure measurement device and method determines blood pressure by sensing pressure waveform data derived from an artery. A pressure sensing device includes a sensing chamber with a diaphragm which is positioned over the artery. A transducer coupled to the sensing chamber senses pressure within the chamber. A flexible body conformable wall is located adjacent to (and preferably surrounding) the sensing chamber. The wall is isolated from the sensing chamber and applies force to the artery while preventing pressure in a direction generally parallel to the artery from being applied to the sensing chamber.

As varying pressure is applied to the artery by the sensing chamber, pressure waveforms are sensed by the transducer to produce sensed pressure waveform data. The varying pressure may be applied automatically in a predetermined pattern, or may be applied manually in a somewhat random fashion.

The sensed pressure waveform data is analyzed to determine waveform parameters which relate to the shape of the sensed pressure waveforms. One or more blood pressure values are derived based upon the waveform parameters.

The Medwave blood pressure measurement devices include both automated devices for continuously monitoring blood pressure (such as in a hospital setting) and hand-held devices which can be used by a physician, or by a patient when desired. These devices represent an important improvement in the field of non-invasive blood pressure measurement. Still further improvements, of course, are highly desirable.

BRIEF SUMMARY OF THE INVENTION

The present invention is an improvement to a non-invasive blood pressure sensing device and method of the type having a fluid filled sensing chamber and a flexible body conformable wall proximate to and isolated from the sensing chamber which applies force to the artery. The present invention is an improvement which minimizes effects of motion artifacts on the blood pressure measurement while maintaining accuracy of blood pressure readings using a constant gain adjustment during pressure pulses.

In the present invention, the flexible body conformable wall includes a chamber which is separate from the sensing chamber. A first transducer senses pressure within the sensing chamber, while a second transducer senses pressure within the chamber which is a part of the flexible body conformable wall.

The signals from the first and second transducers are processed and used to derive pressure waveform data from which blood pressure values are derived. Part of the processing includes the use of an adjusted gain that is substantially constant during heart beats, but that may vary from beat to beat. Signal values obtained from the second transducer are multiplied by the adjusted gain and then subtracted from the signal values obtained from the first transducer. The use of signals from both the first and the second transducers eliminates fluctuations in the signal from the first transducer which are the result of motion artifacts.

BRIEF DESCRIPTION OF THE DRAWINGS

FIGS. 1A–1D show the detail of the LCD display during a pressure measurement cycle.

DETAILED DESCRIPTION

Figure 1:
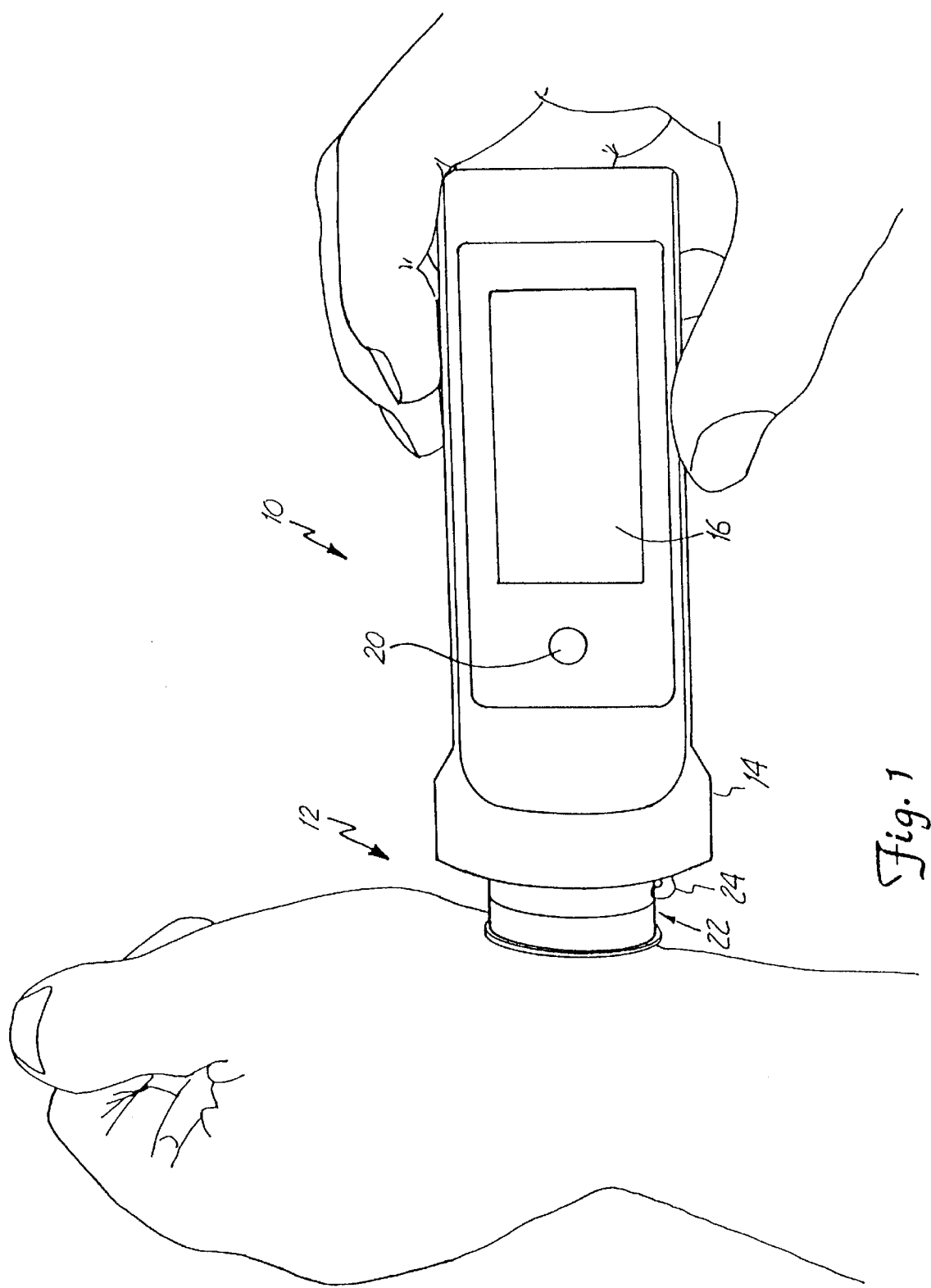
FIG. 1 is a perspective view of a blood pressure measuring device positioned over the wrist of a patient.

FIG. 1 illustrates a hand held blood pressure measurement device being used to measure and display blood pressure within an underlying artery within wrist 12 of a patient. With device 10, a small amount of force is manually applied to the radial artery at the projection of the styloid process bone. As the force is manually applied, blood pressure waveforms are recorded and the corresponding hold down pressure which is being manually applied is also recorded. Using the pressure shape of the blood pressure, waveform parameters are generated. These parameters, along with universal coefficients, are used to calculate pressure values which then can be displayed.

Blood pressure measurement device 10 includes main housing 14, display panel 16, on/off (power) and display select switch 20, sensor interface assembly 22, and connection plug 24.

Housing 14 contains all of the electrical components of measurement device 10. The diameter and length of housing 14 allow it to be easily held by the user (either medical personnel or the patient) during the measurement process. The hold down force is applied by applying force in an axial direction to wrist 12 which is transmitted from housing 14 to sensor interface assembly 22.

Display panel 16 is preferably a liquid crystal display (LCD). In a preferred embodiment, display panel 16 simultaneously displays the following values based upon blood pressure measurements: systolic pressure, diastolic pressure, pulse rate, and mean blood pressure. Display panel 16 also preferably provides visual prompting for manually applying a varying hold down pressure.

Power switch 20 is actuated to turn on power to the circuitry within housing 14. Timing circuitry within housing 14 automatically turns power off after a predetermined period of inactivity. Actuation of switch 20, after the unit is turned on, causes the display to indicate previous readings of blood pressure and pulse rate. In one embodiment there are ten memory locations for readings that can be displayed.

Sensor interface assembly 22 is pivotally mounted to housing 14. As pressure is manually applied by moving housing 14 toward the artery, that force is transferred from housing 14 to sensor interface assembly 22.

In operation, sensor interface assembly 22 is positioned over an artery such as the radial artery (as illustrated in FIG. 1). Alternatively, device 10 can be used in a number of other locations, such as on the temporal artery or the dorsalis pedis artery. The user then begins to apply force to the artery by applying axial force from housing 14 to sensor interface assembly 22. The force applied to the artery is swept in an increasing fashion so that pressure waveform data from a series of pulses are obtained with different amounts of force being applied. To achieve the desired pattern of variable force, user feedback is preferably provided with device 10.

In a preferred embodiment, feedback is in the form of audible tones and/or movable bars on display 16 as shown in FIGS. 1A–1D. Top bar 16A is a pacing bar controlled by the microprocessor. Bottom bar 16B moves in response to the hold down pressure the user applies to the wrist through sensor interface assembly 22. As pressure is applied, bar 16A moves at a fixed rate. The user causes bottom bar 16B to move at approximately the same rate as top bar 16A by applying a steadily increasing force.

The sequence of the measurement cycle is shown in FIGS. 1A–1D. First, the user presses power switch 20, which turns on the device 10. To take a reading, sensor interface assembly 22 is lightly pressed against a pulse locator (as illustrated in FIG. 1) so that bottom bar 16B remains under top bar 16A.

Top bar 16A will start to move across display screen 16. As top bar 16A starts to move, the user must apply increasing pressure through device 10 to the wrist so that bottom bar 16B tracks with the movement of top bar 16A.

Figure 1B:
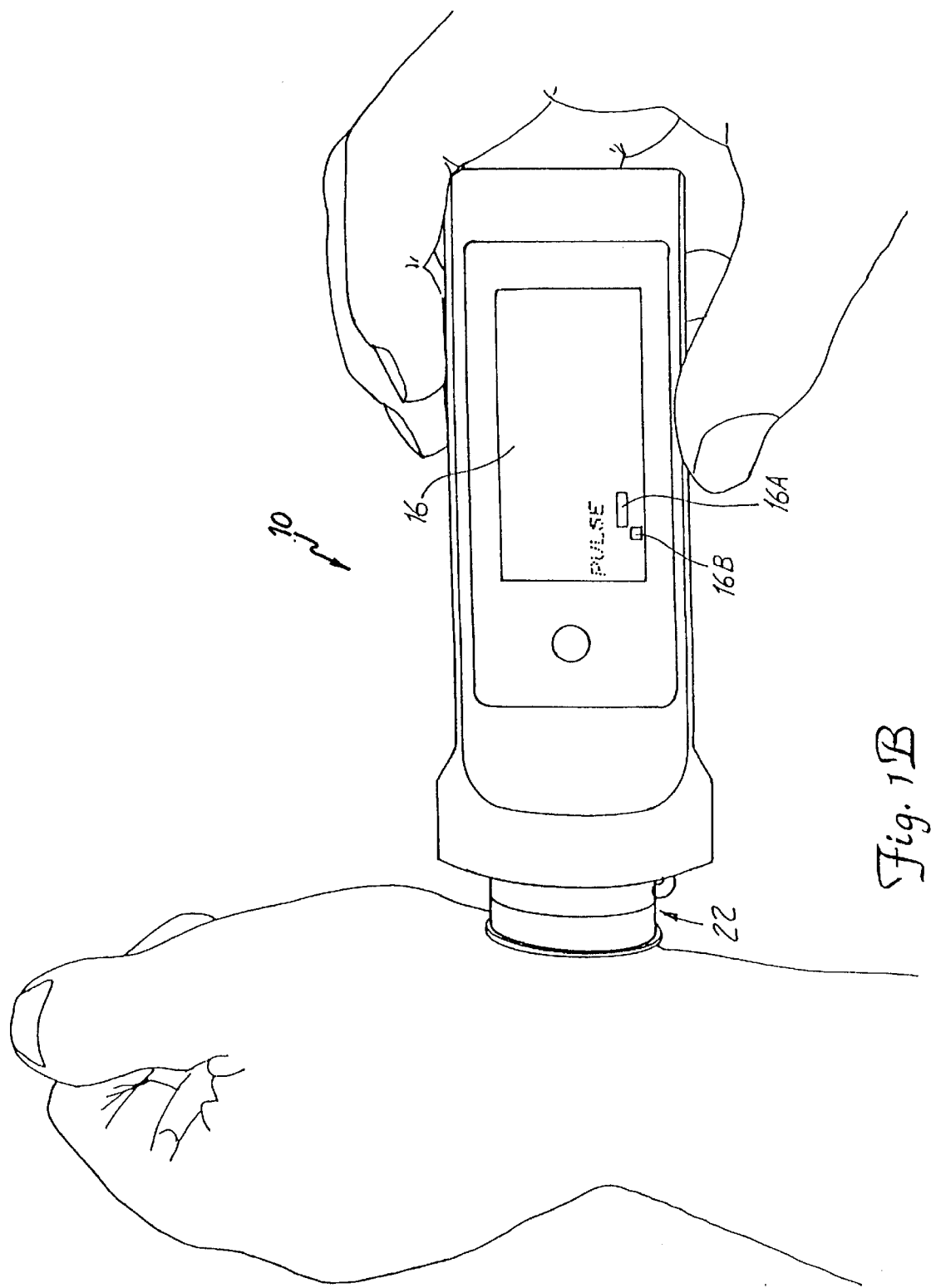

FIG. 1B shows display 16 as top bar 16A has started to move from left to right and bottom bar 16B has not yet begun to track the movement of top bar 16A. FIG. 1C shows bars 16A and 16B as the process continues. Both bars are continuing to move from left to right across the bottom of the display 16. The amount of force required to keep bottom bar 16B underneath top bar 16A will increase as top bar 16A moves across display 16 from left to right.

Figure 1D:
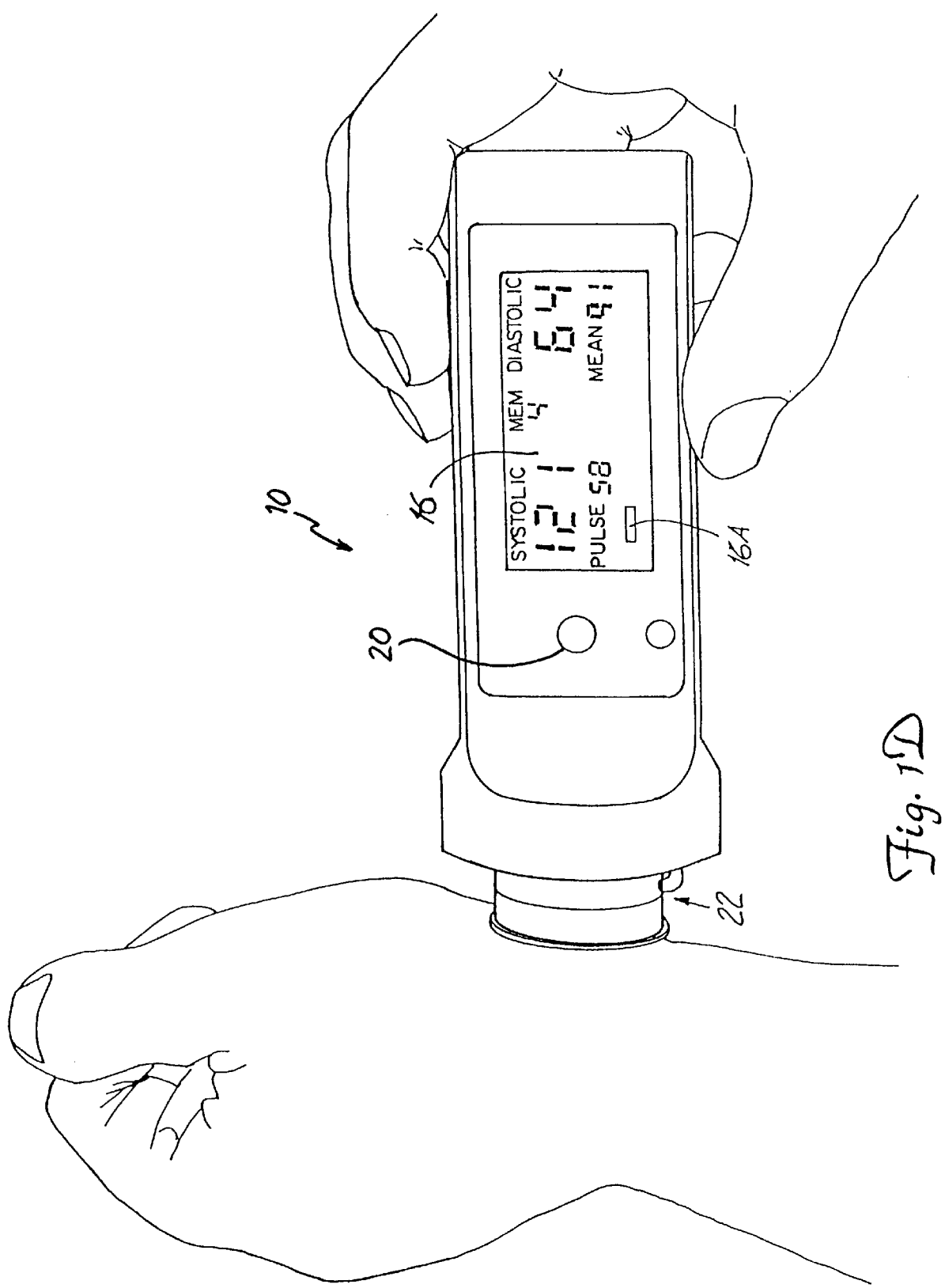

After a beep, the user can remove sensor interface assembly 22 from the wrist. At that point, top bar 16A returns to its left-most position, and bar 16B does not appear on the screen. This is shown in FIG. 1D. The user can then note the blood pressure reading. In a preferred embodiment illustrated in FIG. 1D, display 16 provides a digital readout of systolic, diastolic, and mean blood pressure, as well as pulse rate. An indication of memory location (by number) is also displayed.

As soon as the reading is complete, device 10 is ready to take another reading. There is no need to clear display 16. Device 10 stores a predetermined number of previous readings (such as the last 10 readings). To review prior readings, power switch 20 is pressed. This causes a different reading from memory to be displayed on display 16.

If a tone method is used as feedback, the user applies a force and each tone is modulated and has a higher pitch sound as the amplitude of the cardiac waveform increases. By listening to the tone, the user knows at what rate to apply the pressure to the artery. At the point of maximum energy transfer between the artery and sensor interface assembly 22, the cardiac pressure waveform reaches a peak amplitude and, therefore, the highest frequency tone is produced. As the user continues to apply higher pressure to the artery, the amplitude of the cardiac pressure waveform decreases, and therefore the frequency of the tone decreases. By listening to the tone, the user can perform a variable pressure sweep to measure pressure using device 10.

Feedback to the user can be supplied in other ways as well. For example, an audible tone can be produced using a combination of frequency modulation and amplitude modulation. In other words, as the amplitude of the pressure waveform increases, both pitch (frequency) and amplitude (volume or loudness) of the tone will change.

Figure 2:
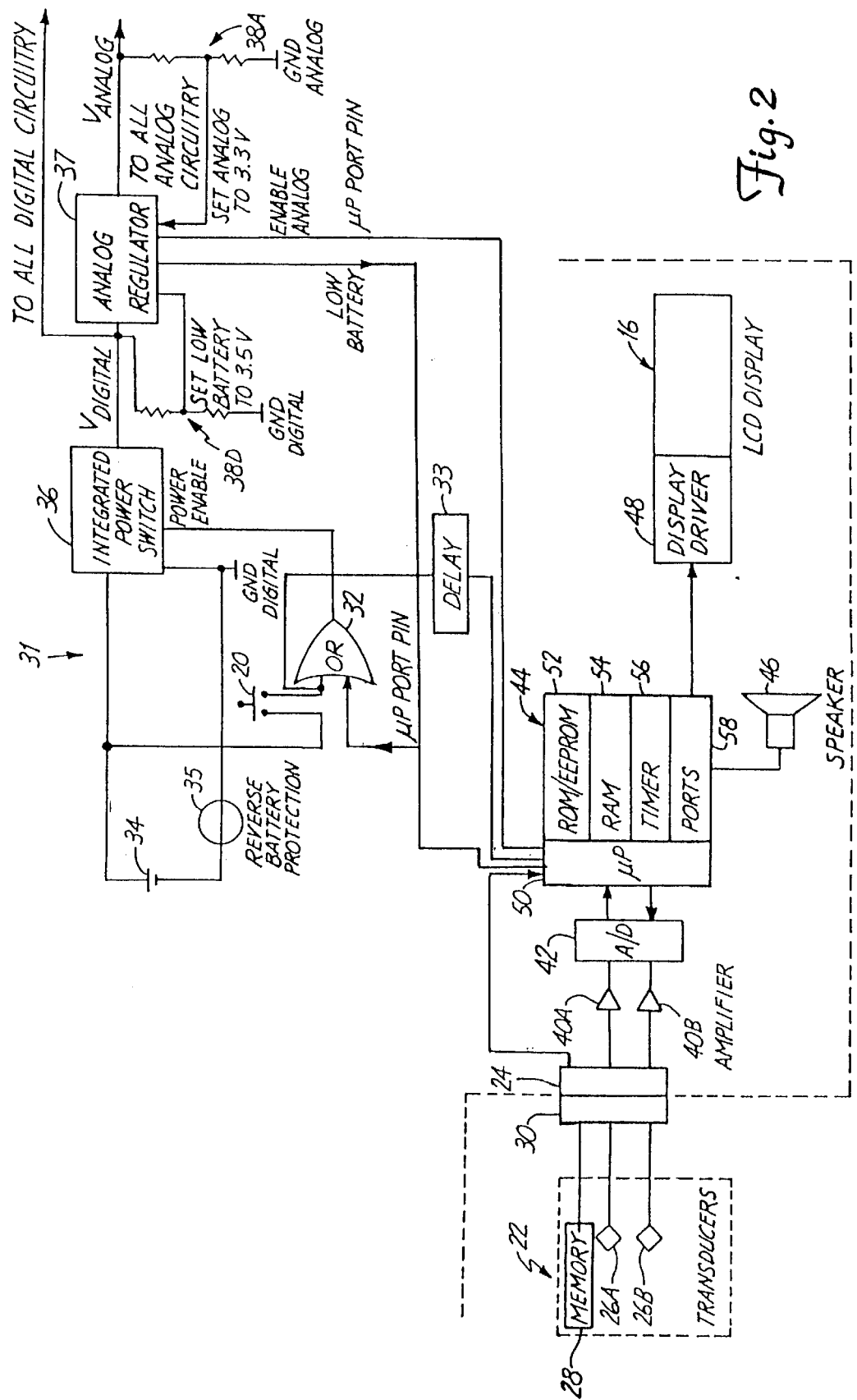
FIG. 2 is an electrical block diagram of the blood pressure measuring device of FIG. 1.

FIG. 2 is an electrical block diagram of device 10. Pressure transducers 26A and 26B and nonvolatile memory 28 within sensor interface assembly 22 are connected through connector 30 and connector 24 to circuitry within housing 14. Power supply circuit 31 includes switch 20, OR circuit 32, delay circuit 33, battery 34, reverse battery protection 35, integrated power switch 36, analog regulator 37, and voltage dividers 38A and 38D. The output of analog regulator 37 is electrical power which is used to energize analog circuitry, which includes amplifiers 40A and 40B, and analog-to-digital (A/D) converter 42. Integrated power switch 36 supplies power to all digital circuits, microprocessor 44, speaker 46, display panel 16 and associated display drive and memory circuitry 48. Microprocessor 44 includes digital signal processing circuitry 50, read only memory (ROM) and electrically erasable programmable read only memory (EEPROM) 52, random access memory (RAM) 54, timer circuitry 56, and input/output ports 58. A/D converter 42 may be integrated with microprocessor 44, while some of the memory may be external to microprocessor 44.

Switch 20 is partially a monitoring pushbutton switch. Pressing switch 20 causes OR circuit 32 to turn on integrated power switch 36. Integrated power switch 36 supplies power to microprocessor 44, which in turn latches on OR circuit 32. The turn off of the circuit is controlled by microprocessor 44 discontinuing a signal to OR circuit 32. This occurs through a fixed time of no activity.

Transducers 26A and 26B sense pressure communicated within sensor interface assembly 22 and supply electrical signals to connector 30. In a preferred embodiment, transducers 26A and 26B are piezoresistive pressure transducers. Nonvolatile memory 28 stores offsets of transducers 26A and 26B and other information such as sensor serial number. Nonvolatile memory 28 is, in a preferred embodiment, an EEPROM.

The outputs of transducers 26A and 26B are analog electrical signals representative of sensed pressure. These signals are amplified by amplifiers 40A and 40B and applied to inputs of A/D converter 42. The analog signals are converted to digital data and supplied to the digital signal processing circuitry 50 of microprocessor 44.

Based upon the pressure data received, microprocessor 44 performs calculations to determine blood pressure values. Those calculations will be described in more detail later. As each pulse produces a cardiac waveform, microprocessor 44 determines a peak amplitude of the waveform. Microprocessor 44 controls display driver 48 to create bars 16A and 16B of FIGS. 1A–1D or drives speaker 46 to produce audible tones which vary as a function of the hold down pressure. The moving bars or audible tones guide the user in applying a variable force to the artery.

When a measurement cycle has been completed, microprocessor 44 reorders the cardiac waveforms in increasing order of their corresponding hold down pressure and performs calculations to determine systolic pressure, diastolic pressure, mean blood pressure, and pulse rate. These values are displayed as shown in FIG. 1D. If switch 20 is pressed while microprocessor 44 is on, a signal is supplied through delay circuit 33 to microprocessor 44, causing it to toggle to a new pressure reading. The memory location of that pressure reading is also displayed, as shown in FIG. 1D.

Figure 3A:
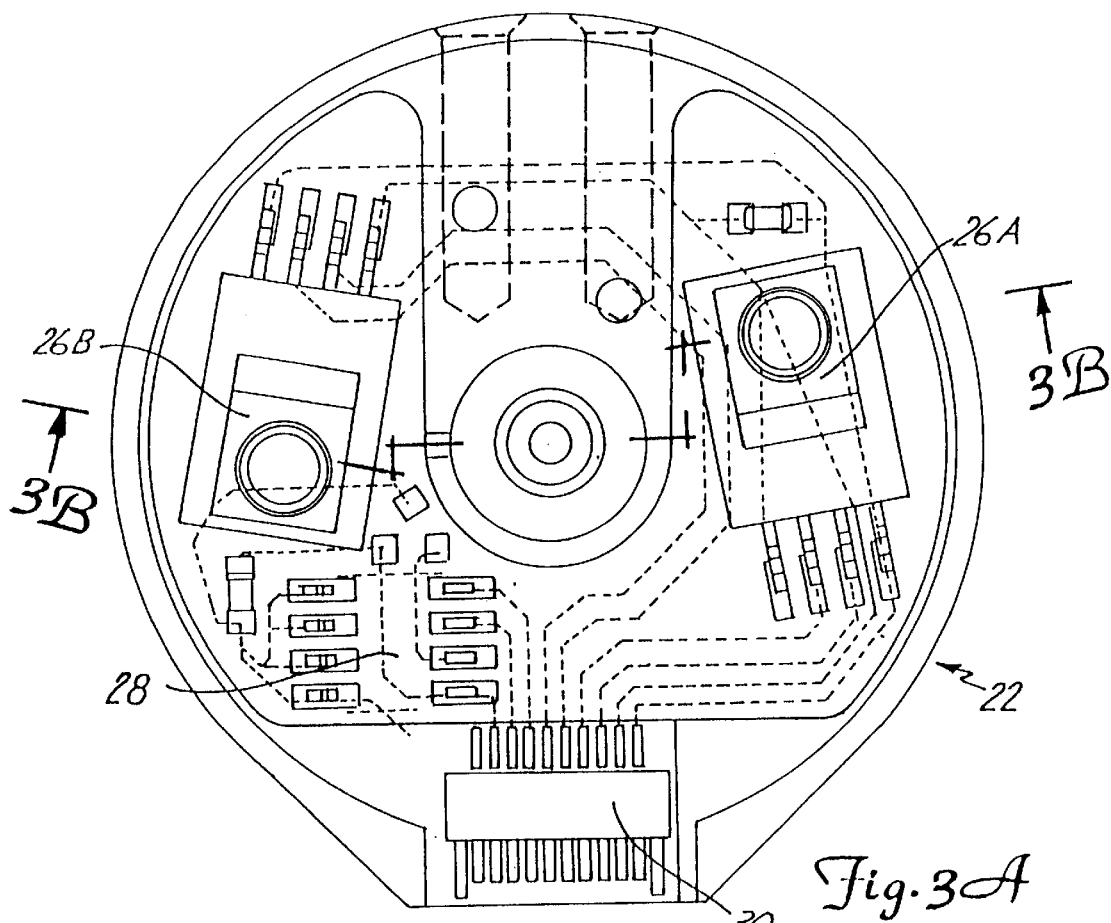
FIG. 3A is a top view of the sensor interface assembly.
Figure 3B:
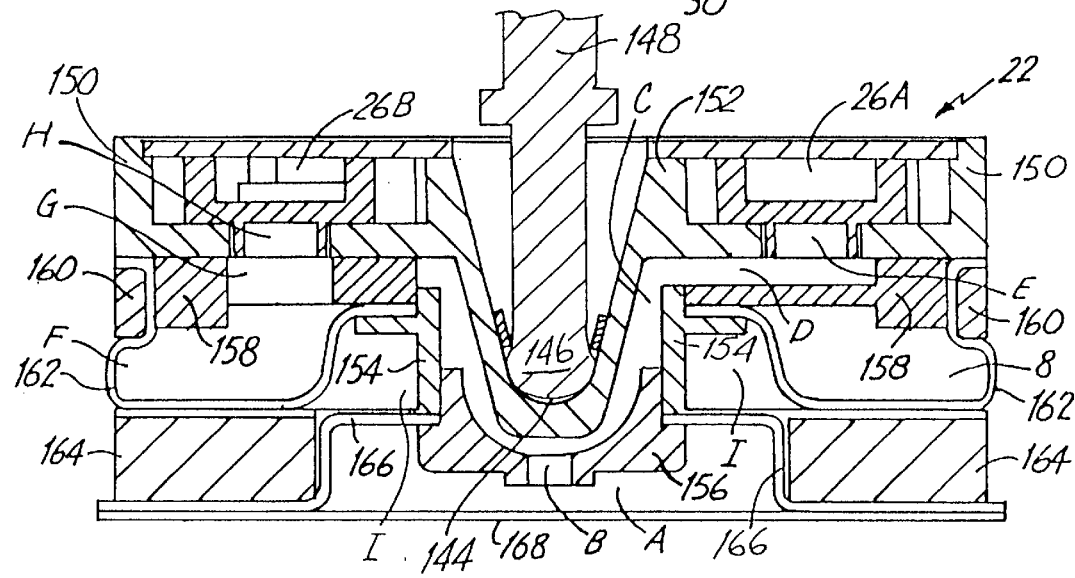
FIG. 3B is a cross-sectional view of the sensor interface assembly along section 3B—3B of FIG. 3A.

FIGS. 3A and 3B illustrate sensor interface assembly 22 in detail. Sensor interface assembly 22 includes top plate 150, upper cup 152, upper capture 154, diaphragm capture 156, inner mounting ring 158, outer mounting ring 160, side wall diaphragm 162, damping ring 164, inner diaphragm 166, and outer diaphragm 168.

As shown in FIG. 3B, transducer 26A measures fluid pressure in fluid-filled sensor chamber A. Channels B, C, D, and E provide fluid pressure communications between transducer 26A and sensor chamber A. Transducer 26B measures fluid pressure in fluid-filled ring chamber F. Channels G and H provide fluid pressure communications between transducer 26B and ring chamber B. Connector 30 communicates with transducers 26A and 26B and non-volatile memory 28.

FIG. 3B also shows how the sensor interface assembly 22 is pivotally connected to housing 14 by a ball 146 and socket 144 arrangement. The ball 146 is pivotally mounted in socket 144. Because sensor interface assembly 22 is pivotally coupled to stem 148 about a low pivot point. This permits sensor interface assembly 22 to be stably positioned above the underlying artery. In addition, the low pivot point enables the user to apply a more direct, uniform force on outer diaphragm 168. Thus, the hold down pressure manually applied by the user (through housing 14 and stem 148) is more uniformly applied to the anatomy above the underlying artery.

Side wall diaphragm 162 and rings 158 and 160 define annular deformable ring chamber F coupled to ring 164. Side wall diaphragm 162 is preferably formed from a generally circular sheet of flexible material, such as polyurethane, and is filled with fluid. Diaphragm 162 has a hole sized to fit around the upper portion of upper capture 154. The outer edge portion of diaphragm 162 is trapped and held between outer ring 160 and top plate 150. The inner edge portion of diaphragm 162 is trapped and supported between ring 158 and upper capture 154. Diaphragm 162 is made from a flexible material and is bulged outward when ring chamber F is filled with fluid. Ring chamber F is compressible and expandable in the vertical direction so as to be able to conform to the anatomy of the patient surrounding the underlying artery. As a result, the distance between top plate 150 and the patient's anatomy can vary around the periphery of side wall diaphragm 162 according to the contour of the patient's anatomy. Furthermore, because fluid is permitted to flow through and around chamber F, pressure is equalized around the patient's anatomy.

Damping ring 164 generally consists of an annular compressible ring and is preferably formed from a foam rubber or other pulse dampening material such as open celled foam or closed cell foam. Ring 164 is centered about and positioned between side wall diaphragm 162 and diaphragms 166 and 168. Damping ring 164 is isolated from the fluid coupling medium within sensor chamber A. Because ring 164 is formed from a compressible material, ring 164 absorbs and dampens forces in a direction parallel to the underlying artery which are exerted by the blood pressure pulses on sensor interface assembly 22 as the blood pressure pulse crosses sensor interface assembly 22. Because bottom ring 164 is isolated from the fluid coupling medium in sensor chamber A, the forces absorbed or received by ring 164 cannot be transmitted to the fluid coupling medium. Instead, these forces are transmitted across ring 164 and side wall diaphragm 162 to top plate 150. Because this path is distinct and separate from the fluid coupling medium, sensor chamber A and the fluid coupling medium are isolated from these forces. In addition, ring 164 also presses tissue surrounding the artery to neutralize or offset forces exerted by the tissue.

Upper diaphragm 166 is an annular sheet of flexible material having an inner diameter sized to fit around diaphragm capture 156. An inner portion of upper diaphragm 166 is trapped or captured (and preferably adhesively affixed) between the lip of diaphragm capture 156 and the bottom rim of upper capture 154.

The intermediate portion of upper diaphragm 166 is adjacent to expansion cavity I and is isolated from ring 164 and ring chamber F. Upper diaphragm 166 is permitted to initially move upward into expansion cavity I as ring chamber F, ring 164, and outer diaphragm 168 conform to the anatomy of the patient surrounding the underlying artery. As ring 164 is pressed against the anatomy of the patient surrounding the artery to neutralize or offset forces exerted by the tissue, outer diaphragm 168 is also pressed against the anatomy and the artery. However, because upper diaphragm 166 is permitted to roll into expansion cavity I, sensor chamber A does not experience a large volume decrease and a large corresponding pressure increase. Thus, sensor interface assembly 22 permits greater force to be applied to the anatomy of the patient through ring 164 to neutralize tissue surrounding the artery without causing a corresponding large change in pressure within sensor chamber A as the height of the side wall changes. As a result, sensor interface assembly 22 achieves more consistent and accurate blood pressure measurements.

Outer diaphragm 168 is a generally circular sheet of flexible material capable of transmitting forces from an outer surface to fluid within sensor chamber A. Outer diaphragm 168 is coupled to inner diaphragm 166 and is configured for being positioned over the anatomy of the patient above the underlying artery. Outer diaphragm sheet 168 includes non-active portion or skirt and an active central portion. The skirt constitutes the area of diaphragm 168 where inner diaphragm 166 is heat sealed or bonded to outer diaphragm 168.

The active portion of outer diaphragm 168 is not bonded to inner diaphragm 166, and is positioned below and within the inner diameter of ring 164. The active portion of outer diaphragm 168 is the active area of sensor interface assembly 22 which receives and transmits pulse pressure to transducer 26A.

The coupling medium within sensor chamber A and passages B–E may consist of any fluid (gas or liquid) capable of transmitting pressure from diaphragm 168 to transducer 26A. The fluid coupling medium interfaces between the active portion of outer diaphragm 168 and transducer 26A to transmit blood pressure pulses to transducer 26A. Because the fluid coupling medium is contained within sensor chamber A and passages B–E, which are isolated from the side wall of sensor interface assembly 22, the fluid coupling medium does not transmit blood pressure pulses parallel to the underlying artery, forces from the tissue surrounding the underlying artery and other forces absorbed by the side wall to transducer 26A. Forces parallel to the underlying artery are dampened by the compressible material of ring 164. As a result, sensor interface assembly 22 more accurately measures and detects arterial blood pressure.

Sensor interface assembly 22 provides external measurements of blood pressure in an underlying artery. Because sensor interface assembly 22 senses blood pressure non-invasively, blood pressure is measured at a lower cost and without medical risks. Because sensor interface assembly 22 is relatively small compared to the larger cuffs used with oscillometric and auscultatory methods, sensor interface assembly 22 applies a hold down pressure to only a relatively small area above the underlying artery of the patient. Consequently, blood pressure measurements may be taken with less discomfort to the patient. Because sensor interface assembly 22 does not require inflation or deflation, faster, more frequent measurement3 may be taken.

Furthermore, sensor interface assembly 22 better conforms to the anatomy of the patient so as to be more comfortable to the patient and so as to achieve more consistent and accurate blood pressure measurements. Because ring chamber F is deformable and filled with fluid, ring chamber F better conforms to the anatomy of the patient and equalizes pressure applied to the patient's anatomy. Because ring 164 is compressible and because outer diaphragm 168 is flexible and is permitted to bow or deform inwardly, ring 164 and outer diaphragm 168 also better conform to the anatomy of the patient. At the same time, however, sensor interface assembly 22 does not experience a large sudden increase in pressure in sensor chamber A as ring 164 and outer diaphragm 168 are pressed against the anatomy of the patient. Ring chamber F and ring 164 apply force to the anatomy of the patient to neutralize the forces exerted by tissue surrounding the underlying artery. Because ring chamber F and ring 164 are both compressible in height, the height of the side wall decreases as the side wall is pressed against the patient. Diaphragms 166 and 168 arc also conformable. However, because the intermediate portion of inner diaphragm 166 is permitted to move upward into expansion cavity I, sensor chamber A does not experience a large volume decrease and a corresponding large pressure increase. Thus, the side wall is able to apply a greater force to the anatomy of the patient without causing a corresponding large, error-producing increase in pressure within sensor chamber A due to the change in height of the side wall and the change in shape of outer diaphragm 168.

At the same time, sensor interface assembly 22 permits accurate and consistent calculation of blood pressure. Because of the large sensing area through which blood pressure pulses may be transmitted to transducer 26A, sensor interface assembly 22 is not as dependent upon accurate positioning of the active portion of outer diaphragm 168 over the underlying artery. Thus, sensor interface assembly 22 is more tolerant to patient movement as measurements are being taken.

Moreover, sensor interface assembly 22 achieves a zero pressure gradient across the active face of the sensor, achieves a zero pressure gradient between the transducer and the underlying artery, attenuates or dampens pressure pulses that are parallel to the sensing surface of the sensor, and neutralizes forces of the tissue surrounding the underlying artery. Sensor interface assembly 22 contacts and applies force to the anatomy of the patient across the skirt and the active portion of outer diaphragm 168. However, the pressure within sensor chamber A is substantially equal to the pressure applied across the active portion of outer diaphragm 168. The remaining force applied by sensor interface assembly 22 across the skirt, which neutralizes or offsets forces exerted by the tissue surrounding the underlying artery, is transferred through the side wall (ring 164 and ring chamber F) to top plate 150. As a result, the geometry and construction of sensor interface assembly 22 provides the proper ratio of pressures between the skirt and the active portion of outer diaphragm 168 to neutralize tissue surrounding the underlying artery and to accurately measure the blood pressure of the artery. In addition, because the fluid coupling medium within sensor chamber A is isolated from the side wall, pressure pulses parallel to the underlying artery, forces from tissue surrounding the underlying artery, and other forces absorbed by the side wall are not transmitted through the fluid coupling medium to transducer 26A. Consequently, sensor interface assembly 22 also achieves a zero pressure gradient between transducer 26A and the underlying artery.

Blood pressure measuring device 10 determines blood pressure values from the sensed waveform pressure amplitudes sensed by sensor interface assembly 22 and from other parameters derived from the pressure amplitudes using a stored set of coefficients. A pressure amplitude is determined at each sample point.

Device 10 calculates a systolic blood pressure value (S), a mean blood pressure value (M) and a diastolic blood pressure value (D) based upon the following formulas:

$$M = F_m(P_1^m, \ldots, P_n^m, C_1^m, \ldots C_n^m)$$

$$S = F_s(P_1^s, \ldots, P_n^s, C_1^s, \ldots C_n^s)$$

$$D = F_d(P_1^d, \ldots P_n^d, C_1^d, \ldots C_n^d)$$

wherein $F_m$, $F_s$, $F_d$ are linear or non-linear functions, $P_1^m$, $P_1^s$, $P_1^d$, ... $P_n^m$, $P_n^s$, $P_n^d$ are parameters derived from waveform pressure amplitudes, and $C_1^m$, $C_1^s$, $C_1^d$, ..., $C_n^m$, $C_n^s$, $C_n^d$ are coefficients obtained during training processes based upon clinical data.

In particular, device 10 calculates a systolic blood pressure value (S), a mean blood pressure value (M), a diastolic blood pressure value (D) based upon the following formulas:

$$M = C_1^m P_1^m + C_2^m P_2^m + \ldots + C_n^m P_n^m$$

$$S = C_1^s P_1^s + C_2^s P_2^s + \ldots + C^{ns} P_n^s$$

$$D = C_1^d P_1^d + C_2^d P_2^d + \ldots + C_n^d P_n^d$$

wherein $P_1^m$, $P_1^s$, $P_1^d$ ... $P_n^m$, $P_n^s$, $P_n^d$ are parameters derived from waveform pressure amplitudes. Such parameters may be calculated from shape characteristics of the waveform or parameters calculated from functions such as curves based upon relationships between particular points of several waveforms. The parameters may be further based upon hold down pressure values and time periods between particular points on the waveforms. The values $C_1^m$, $C_1^s$, $C_1^d$ ... $C_n^m$, $C_n^s$, $C_n^d$ are coefficients obtained during training processes based upon clinical data.

In addition, the pulse rate (PR) may also be determined using the formula:

$$PR = \frac{PR_1 + PR_2 + PR_3 + PR_4}{4}$$

To determine the pulse rate, four individual waveforms, or beats, are sensed and are time averaged to determine the pulse rate. Preferably, the waveforms used to determine pulse rates include the waveform having the largest maximum pressure amplitude, the two waveforms prior to the waveform having the largest maximum pressure amplitude and the waveform succeeding the waveform having the largest maximum pressure amplitude. Once the four waveforms are identified, the pulse rate of each waveform is determined. The sum of the pulse rate of the four waveforms is then divided by four to calculate pulse rate PR. The pulse rate (PR) for each waveform is based upon the following formula:

$$PR_N \text{ beats per minute}(N = 1, 2, 3, 4) = \frac{128 \text{ samples/sec}}{\text{No. samples/beat}_N} \times 60 \text{ sec/min}$$

Figure 4:
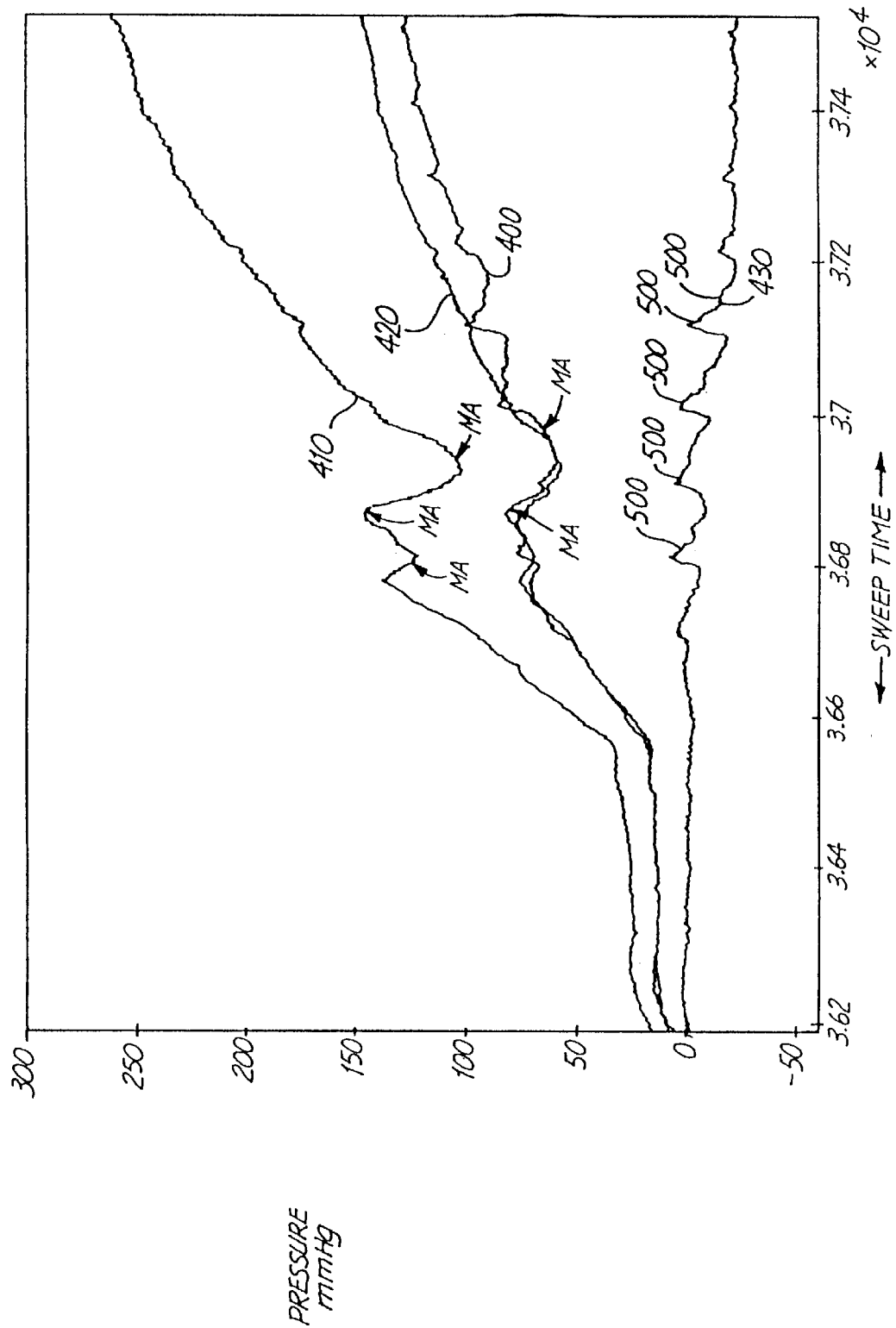
FIG. 4 is a graph illustrating blood pressure waveforms.

FIG. 4 illustrates a sample series of waveforms exhibited by the underlying artery as a varying pressure is applied over time. The vertical scale indicates pressure in mmHg while the horizontal scale indicates individual sample points at which the blood pressure values exerted by the pulse are measured over time. In the preferred embodiment, transducers 26A and 26B produce continuous electrical signals representing waveform pressures which are sampled 128 times per second.

In the preferred embodiment, the hold down pressure applied to sensor interface assembly 22 is swept over a preselected range of increasing hold down pressures. Preferably, the sweep range of hold down pressures typically is begun at approximately 10 mmHg. The hold down pressure is then steadily increased (under the prompting or guidance from the audible or visual feedback) until two individual waveforms are sensed following the sensed waveform having the largest pressure amplitude. Preferably, each sweep range extends between an initial hold down pressure of about 10 mmHg and a final hold down pressure of approximately 150% of the mean hold down pressure of the waveform having the largest maximum pressure amplitude during the previous sweep.

FIG. 4 shows the signals 400 and 410 from transducers 26A and 26B, respectively, as sensor interface assembly 22 is pressed against the artery. Signal 400 is representative of pressure in sensor chamber A. Signal 410 represents the pressure in ring chamber F as sensed by transducer 26B. Signal 420 is representative of pressure in ring chamber F after applying a proper gain and offset. Signal 410 is calibrated to match signal 400. This gain and offset adjustment can take place in an initial phase of a pressure measurement. This gain and offset adjustment can also take place on a continual basis or at any other phase of a pressure sweep. A least square fit can be used to find the best fit of curves 400 and 410 so as to get the best gain and offset adjustment.

At multiple places during the sweep, signals 400 and 420 are affected by patient movement or (in the case of a hand-held blood pressure unit) operator movement as the sweep is performed. These inflections or motion artifacts MA show noise that needs to be taken out of the system in order to measure blood pressure. Signal 430 has most of the noise taken out of signal 400, and is referred to as a "clean" signal. Signal 430 contains pressure pulse waveforms 500 from the movement of the arterial walls as sensor interface assembly 22 is pressed against the arterial wall.

Figure 5:
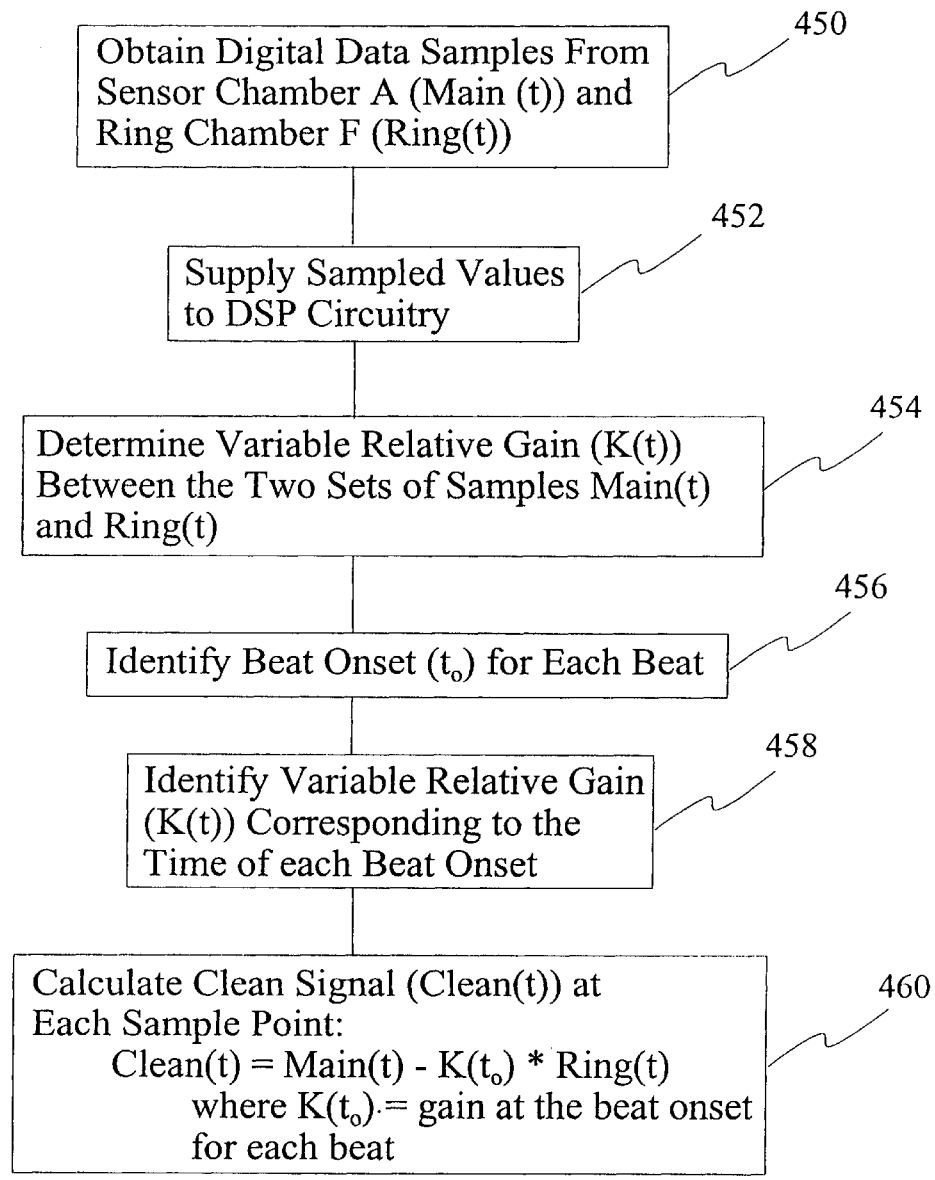
FIG. 5 is a flow diagram of a preferred process for calculating clean signal values.

FIG. 5 shows a summary of a preferred process for calculating "clean" signal values, which are the values used to construct curve 430 shown in FIG. 4. The first step shown in FIG. 5 is to obtain digital data samples from sensor chamber A and ring chamber F. (Block 450). The samples from sensor chamber A are represented by "main(t)", and the samples obtained from ring chamber F are represented by "ring(t)", where "t" represents the time at which each sample was taken. The digital data samples from sensor chamber A (i.e., main(t)) are represented graphically in FIG. 4 as curve 400. The digital data samples from ring chamber F (i.e., ring(t)) are represented graphically in FIG. 4 as curve 410.

As digital data samples are obtained, they are supplied to digital signal processing circuitry 50 of microprocessor 44. (Block 452). Preferably, digital signal processing circuitry 50 determines the variable relative gain (K(t)) between the main(t) values and the ring(t) values at each sample point. (Block 454). The variable relative gain between sample points may be calculated while digital data samples are being obtained. In contrast, using the least square fit method typically requires that all of the samples be obtained for a particular pressure sweep prior to calculating the variable relative gain.

Figure 6:
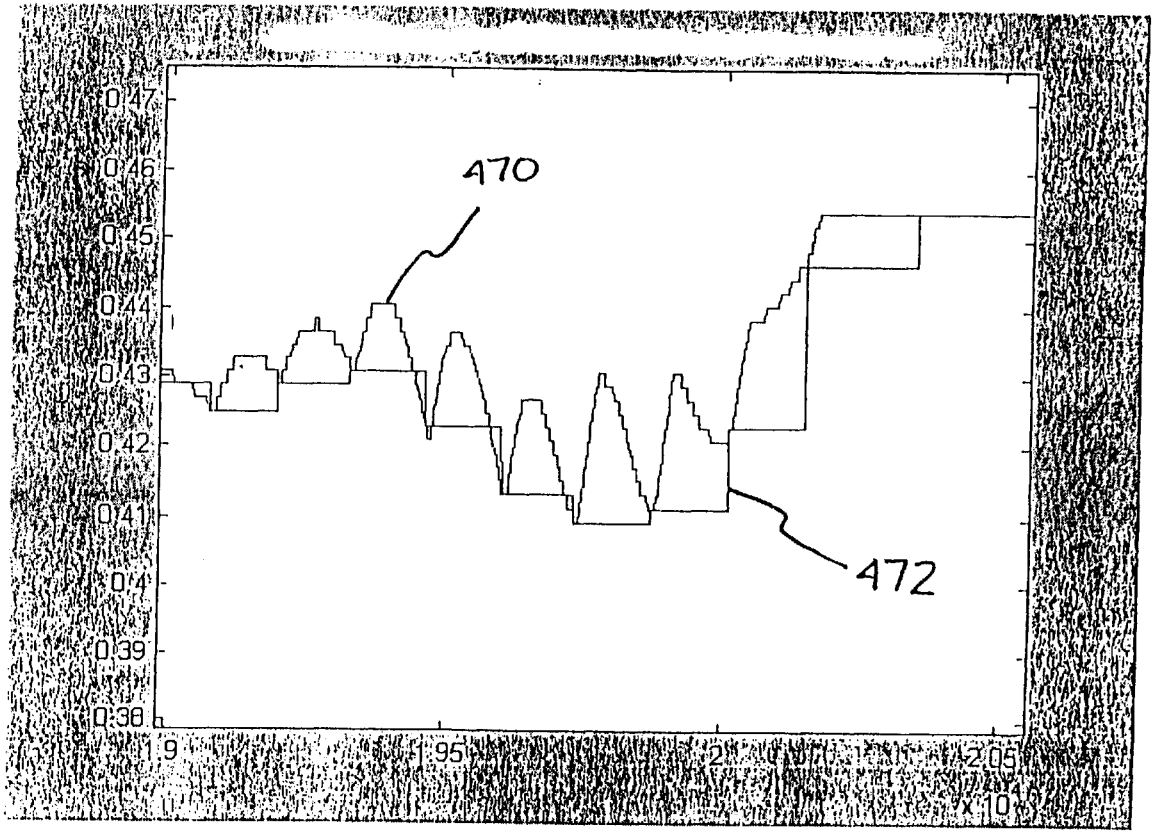
FIG. 6 is a graph of variable gain and adjusted gain as a function of time.

The ring(t) values are multiplied by the gain coefficients K(t) to obtain the values for signal 420. In a preferred embodiment, only a subset of the gain coefficients are used in adjusting curve 410 to obtain the values for curve 420. Specifically, only the gain coefficients with time values t that correspond to the beginning of each pressure pulse waveform or beat are used. These values are then held constant during the beat to generate an adjusted gain 472. FIG. 6 shows a graph of the variable gain coefficients 470 and the adjusted gain 472 versus time. In alternative preferred embodiments, the abrupt step changes in gain between beats in curve 472 are eliminated, and the transitions in gain between beats are made smooth. By smoothing the transitions in curve 472, the gain still remains substantially constant during each beat.

The digital data samples ring(t) are preferably multiplied by the adjusted gain 472 to obtain the values for curve 420. The adjusted gain 472, rather than gain 470, is used in adjusting curve 410, because, in minimizing the error between curve 400 and curve 410, the variable gain method views the pressure pulse waveforms on signal 400 as errors that need to be minimized. However, the pressure pulse waveforms are actually signal values, and not errors.

The next step in the process for generating "clean" signal values (curve 430) is to identify the time at the beginning of each beat, or the beat onset ($t_0$), for each beat in curve 400. (Block 456). Commonly-assigned U.S. Patent No. 5,720, 292, entitled "BEAT ONSET DETECTOR", discloses a preferred method for detecting the onset of heart beats. The variable relative gain (K(t)) corresponding to the time of each beat onset is identified. (Block 458). Lastly, the "clean" signal values (curve 430) are obtained for each sample point using the equation:

$$\text{clean}(t) = \text{main}(t) - K(t_0) \times \text{ring}(t)$$

where:
clean(t) represents the digital data values for curve 430;
main(t) represents the values for curve 400;
ring(t) represents the values for curve 410; and
$K(t_0)$ represents the variable relative gain at the beat onset for each beat. (Block 460).

It has been determined that keeping the gain constant during each beat (i.e., using the adjusted gain 472 rather than gain 470) in calculating the values for curve 430 helps to minimize the distortion of the shape of each "clean" beat 500. Minimizing the distortion of the shape of each beat is important because, as discussed below, various parameters may be obtained based on the shape of these beats. For example, one parameter that is affected by the gain adjustment is the tail segment length parameter, which is illustrated in FIG. 7.

Figure 7:
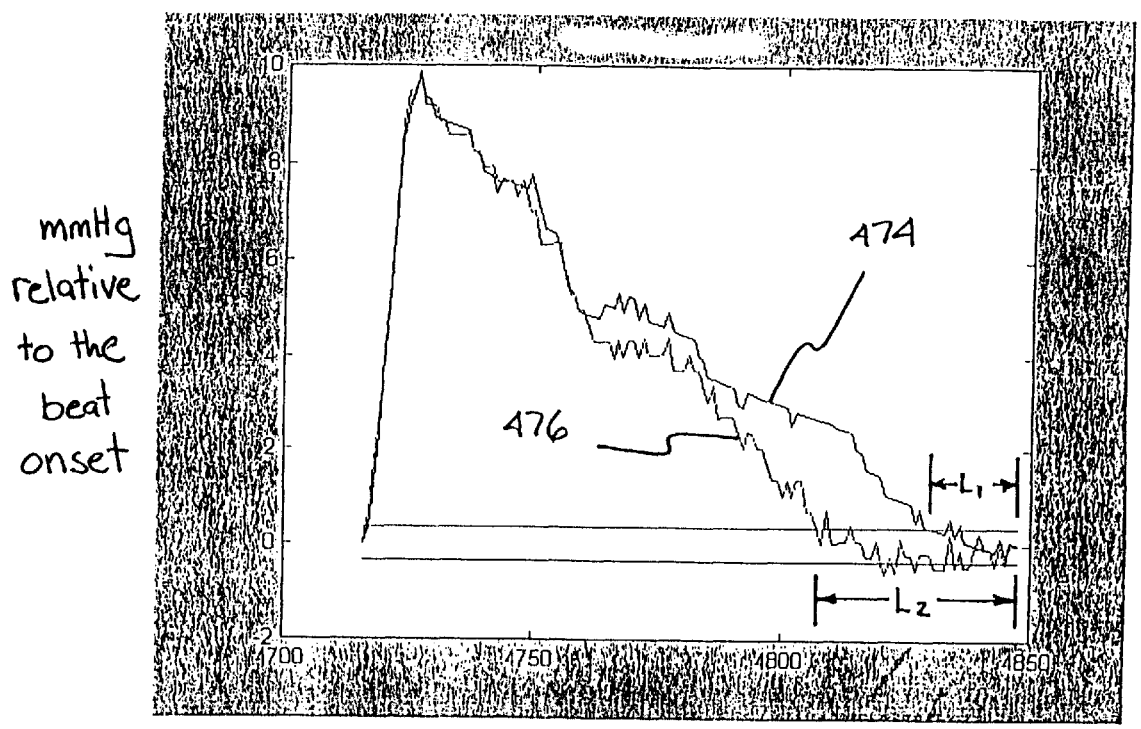
FIG. 7 is a graph illustrating a pressure waveform obtained using a variable gain.

FIG. 7 shows waveform 474, which is a normalized graph of a pressure waveform taken from curve 400, and also shows waveform 476, which is a normalized graph of one of clean pressure waveforms 500 taken from curve 430, where curve 430 was calculated using the variable gain coefficients 470 shown in FIG. 6. The tail segment length parameter represents the length of the flat portion at the end of each pressure waveform. For pressure waveform 474, the tail segment length parameter is represented by $L_1$, and for pressure waveform 476, the tail segment length parameter is represented by $L_2$. The tail segment length parameter is a distortion parameter taken from the pressure waveform occurring before the pressure waveform with the maximum amplitude.

As shown in FIG. 7, when the variable gain coefficients 470 are used in calculating curve 430, the tail of the pressure waveform 476 becomes longer than the tail of pressure waveform 474. When the tail segment length parameter is used in calculating diastolic blood pressure, it has been determined that the increased value of the tail segment length parameter causes the calculated diastolic blood pressure to be slightly lower than readings obtained from an arterial line. The tail segment length parameter is over estimated due to the fact that the variable gain is adapting every sample and is thereby causing the end of each pressure waveform to be a little flatter and longer.

Figure 8:
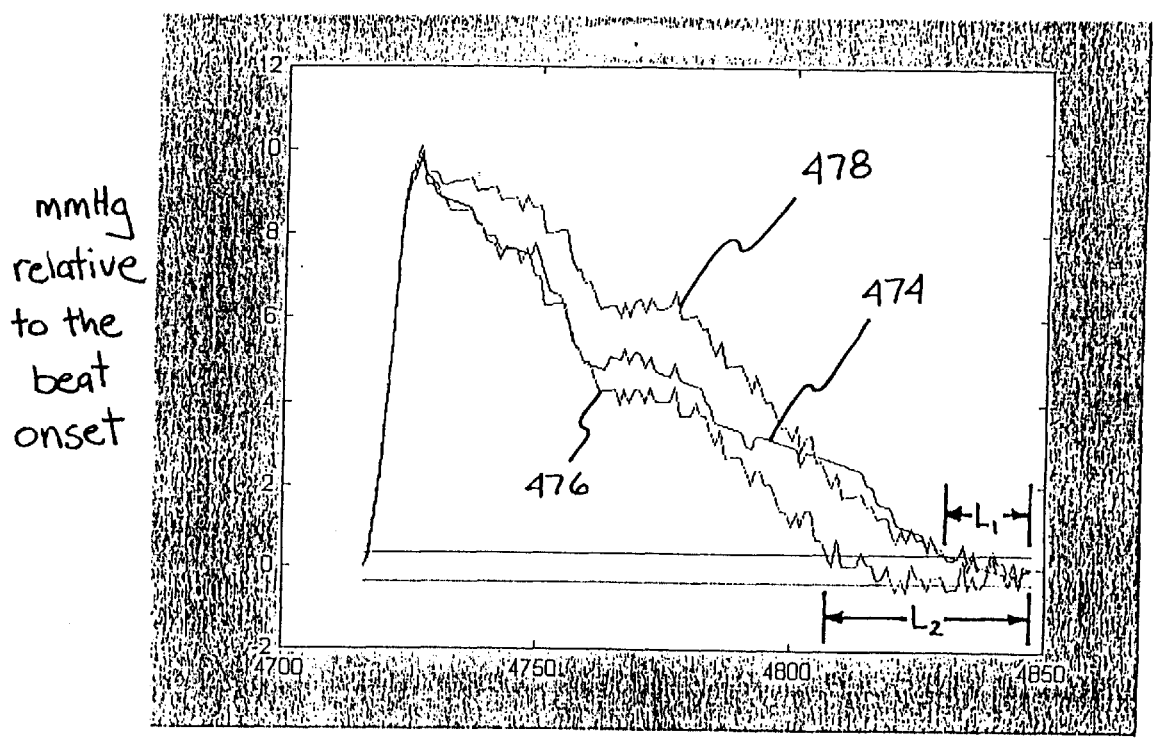
FIG. 8 is a graph illustrating a pressure waveform obtained using a variable gain, and a pressure waveform obtained using an adjusted gain.

By using adjusted gain 472 rather than gain 470 in calculating curve 430, a more accurate tail segment length parameter is obtained. FIG. 8 shows a graph of waveform 478, which is a normalized graph of a pressure waveform obtained directly from a patient's artery. As can be seen in FIG. 8, the tail segment length parameter of waveform 478 is virtually identical to the tail segment length parameter L, of waveform 474. By using the tail segment length parameter from waveform 478 in calculating diastolic blood pressure, the calculated blood pressure value more closely approaches the value obtained from the arterial line method. More accurate values are also obtained for systolic and mean blood pressure when parameters are derived from waveform 478 rather than waveform 476.

Signal 430 represents blood pressure pulses that can be used to obtain shape and amplitude information to calculate blood pressure. Signal 400 can be used to obtain additional information such as hold down pressure that is also used to calculate pressure.

As can be observed in FIG. 4, when noise causes signal 400 to sweep in a non-uniform movement, it may be required to reorder the beats in order of increasing hold down pressure in order to calculate blood pressure.

Based upon sensed and sampled pressure waveform signals or data produced by transducers 26A and 26B during each sweep of hold down pressures, microprocessor 44 derives preselected parameters for calculating blood pressure values from the derived parameters and a stored set of coefficients. As indicated in FIG. 4, parameters may be derived directly from the absolute waveform pressures which vary as hold down pressure is varied over time. Such parameters may be derived from the shape of the waveforms including a particular waveform's slope, absolute pressure at a selected sample point, a rise time to a selected sample point on a waveform, and the hold down pressures corresponding to a particular sample point on a waveform. As can be appreciated, any of a variety of parameters may be derived from the absolute waveform pressures shown in FIG. 4. Parameters may further be based upon particular points or functions of the sample points.

A preferred process of calculating pressure using shape, amplitude, and hold down is described in commonly-assigned U.S. patent application Ser. No. 08/912,139, filed Aug. 15, 1997, entitled HAND-HELD NON-INVASIVE BLOOD PRESSURE MEASUREMENT DEVICE, and U.S. Pat. No. 5,797,850, entitled METHOD AND APPARATUS FOR CALCULATING BLOOD PRESSURE OF AN ARTERY, which are incorporated by reference.

In preferred embodiments of the present invention, the waveform analysis described in U.S. Pat. No. 5,738,103 entitled "Segmented Estimation Method" and U.S. Pat. No. 5,720,292 entitled "Beat Onset Detector" are also used.

Although the present invention has been described with reference to preferred embodiments, workers skilled in the art will recognize that changes may be made in form and detail without departing from the spirit and scope of the invention. For example, although the determination of pressure values based upon waveform parameters has been described using linear equations and stored coefficients, other methods using non-linear equations, look-up tables, fuzzy logic and neural networks also can be used in accordance with the present invention.

In other embodiments, algorithms can be used that compensate for a nonlinear hold down pressure sweep. This is accomplished by recording hold down pressure and pulse shape, so that the operation does not perform a linear sweep. A linear sweep can be constructed as long as there are several pulse shapes recorded over the range of the sweep, regardless of the order they are recorded.

What is claimed is:

1. A method for determining blood pressure of an artery having a pulse, the method comprising:

applying pressure to the artery;

sensing pressure data produced by the artery, the pressure data including data for a plurality of beats;

sensing noise data;

adjusting the noise data with a gain having a substantially fixed value during each beat, the gain being variable from beat to beat;

correcting the pressure data based upon the noise data to produce corrected pressure data;

deriving a plurality of parameters from the corrected pressure data; and determining a blood pressure value based upon the parameters.

2. The method of claim 1 wherein sensing noise data comprises sensing pressure applied to the artery.

3. A method for determining blood pressure of an artery, the method comprising:
   applying pressure to the artery so that the artery exhibits a plurality of pressure waveforms;
   producing sensed pressure waveform data representing each of the plurality of pressure waveforms;
   producing noise data which is representative of noise contained in the pressure waveforms;
   correcting the noise data by a function which may vary from pressure waveform to pressure waveform and which is a substantially fixed value during each pressure waveform;
   correcting the sensed pressure waveform data based on the noise data to produce corrected pressure waveform data;
   deriving a plurality of parameters from the corrected pressure waveform data; and
   determining a blood pressure value based upon the parameters.

4. The method of claim 3 wherein the function is a gain.

5. A non-invasive blood pressure measurement device, the measurement device comprising:
   means for applying pressure to an artery so that the artery exhibits pressure data;
   first sensing means for sensing the pressure data, the pressure data including data for a plurality of bears;
   second sensing means for sensing noise data;
   signal producing means connected to the first and second sensing means for producing output signals corresponding to the sensed pressure data; and
   processing means for receiving the output signals from the signal producing means, for deriving a plurality of parameters using sensed pressure corrected to remove noise, the noise adjusted with a gain having a substantially fixed value during each beat, the gain being variable from beat to beat, and for determining a blood pressure value using the derived parameters.

6. The measurement device of claim 5 wherein the first sensing means includes:
   a first transducer having a sensing surface;
   a first flexible diaphragm for being positioned over the underlying artery; and
   first interface means between the first flexible diaphragm and the sensing surface of the transducer for transmitting pressure pulses from the diaphragm to the transducer.

7. The measurement device of claim 6 wherein the second sensing means includes:
   a second diaphragm which is responsive to pressure applied to the artery;
   a second transducer; and
   second interface means between the second diaphragm and the second transducer for transmitting pressure from the diaphragm to the second transducer.

8. The measurement device of claim 7 wherein the first and second sensing means arc mounted on a sensor interface assembly which is pivotally connected to a housing.

9. A non-invasive blood pressure measurement system comprising:
   means for applying pressure to an artery;
   means for sensing pressure from the artery over time while the pressure is applied to the artery to generate pressure data, the pressure data including data for a plurality of beats;
   means for sensing noise associated with applying pressure;
   means for adjusting the noise with a gain having a substantially fixed value during each beat, the gain changing between beats;
   means for deriving a pressure value based upon a waveform analysis of the pressure data as corrected with the noise data.

10. A method of determining blood pressure, the method comprising:
    applying pressure to an artery;
    sensing pressure over time while pressure is applied to the artery to generate pressure waveform data for pressure waveforms representing a plurality of beats;
    sensing noise over time;
    correcting the noise by a gain which may vary from beat to beat and which is a substantially fixed value during each beat;
    correcting the waveform data to remove the corrected noise;
    detecting onset of the beats from the waveform data;
    extracting waveform parameters using a detected onset of one of the beats; and
    determining a blood pressure value based upon the waveform parameters.

11. A method for determining blood pressure of an artery having a pulse, the method comprising:
    applying pressure to the artery;
    sensing pressure data produced by the artery, the pressure data including data for a plurality of beats;
    correcting the pressure data by removing noise components associated with motion artifacts, the noise components adjusted with a gain having a substantially fixed value during each beat, the gain variable from beat to beat;
    deriving a plurality of parameters from the corrected pressure data; and
    determining a blood pressure value based upon the plurality of parameters and a stored set of coefficients.

12. A device for external measurements of blood pressure in an underlying artery surrounded by tissue of a patient, the device comprising:
    first sensing means for sensing blood pressure pulses in the underlying artery;
    second sensing means for sensing noise associated with motion artifacts;
    means for adjusting the noise with a gain having a substantially fixed value during each pulse, the gain changing between pulses;
    means for applying a variable pressure to the artery; and
    means for calculating blood pressure from the sensed blood pressure pulses corrected to remove the adjusted noise, based upon shape of the sensed pressure pulses within the underlying artery.

13. The device of claim 12 wherein the first sensing means includes:
    a first transducer having a sensing surface;
    a first flexible diaphragm for being positioned over the underlying artery; and first interface means between the first flexible diaphragm and the sensing surface of the first transducer for transmitting pressure pulses from the first flexible diaphragm to the first transducer.

14. The device of claim 13 wherein the second sensing means includes:
   a second transducer having a sensing surface;
   a second flexible diaphragm; and
   second interface means between the second flexible diaphragm and the sensing surface of the transducer for transmitting pressure from the second flexible diaphragm to the second transducer.

15. A method of generating adjusted pressure waveform data representing blood pressure pulses in an artery, the method comprising:
   sensing a range of pressures applied to the artery and generating pressure data that represents the sensed pressures;
   sensing the blood pressure pulses in the artery and generating pulse data that represents the sensed blood pressure pulses;
   calculating relative gain values representing the relative gain between the pressure data and the pulse data at various points in time;
   adjusting the pressure data with a function based on the relative gain values, the function varying between pulses and held substantially constant during each pulse; and
   generating adjusted pressure waveform data by subtracting the adjusted pressure data and the pulse data.

16. The method of claim 15 wherein the function is a gain.

17. The method of claim 16 and further comprising:
   deriving a plurality of parameters from the adjusted pressure waveform data; and
   determining a blood pressure value based upon the plurality of parameters.

18. A non-invasive blood pressure measurement device, the measurement device comprising:
   means for applying pressure to an artery so that the artery exhibits pressure data;
   first sensing means for sensing the pressure data, the pressure data including data for a plurality of beats, wherein the first sensing means includes:
      a first transducer having a sensing surface;
      a first flexible diaphragm for being positioned over the underlying, artery; and
         first interface means between the first flexible diaphragm and the sensing surface of the transducer for transmitting pressure pulses from the diaphragm to the transducer;
   second sensing means for sensing noise data;
   signal producing means connected to the first and second sensing means for producing output signals corresponding to the sensed pressure data; and
   processing means for receiving the output signals from the signal producing means, for deriving a plurality of parameters using sensed pressure corrected to remove noise, the noise adjusted with a gain having a substantially fixed value during each beat, and for determining a blood pressure value using the derived parameters.

19. The measurement device of claim 18 wherein the second sensing means includes:
   a second diaphragm which is responsive to pressure applied to the artery;
   a second transducer; and
   second interface means between the second diaphragm and the second transducer for transmitting pressure from the diaphragm to the second transducer.

20. The measurement device of claim 19 wherein the first and second sensing means are mounted on a sensor interface assembly which is pivotally connected to a housing.

* * * * *

UNITED STATES PATENT AND TRADEMARK OFFICE
CERTIFICATE OF CORRECTION

PATENT NO. : 6,245,022 B1
DATED : June 12, 2001
INVENTOR(S) : G. Kent Archibald et al.

It is certified that error appears in the above-identified patent and that said Letters Patent is hereby corrected as shown below:

Column 13,
Line 32, delete "bears", insert -- beats --
Line 64, delete "arc", insert -- are --

Signed and Sealed this

Twelfth Day of March, 2002

Attest:

Attesting Officer

JAMES E. ROGAN
Director of the United States Patent and Trademark Office